United States Patent [19]

Hermecz et al.

[11] 4,395,549
[45] Jul. 26, 1983

[54] 6-HYDRAZONO-PYRIDO[2,1-B] QUINAZOLINE-11 ONES

[75] Inventors: Istvan Hermecz, Budapest; Jozsef Kökosi, Budaörs; Agnes Horvath, Budapest; Zoltan Meszaros, Budapest; György Szasz, Budapest; Tibor Breining, Budapest; Lelle Vasvari nee Debreczy, Budapest, all of Hungary

[73] Assignee: Chinoin Gyogyszer es Vegyeszeti Termekek Gyara Rt., Budapest, Hungary

[21] Appl. No.: 308,038

[22] Filed: Oct. 2, 1981

[51] Int. Cl.³ .................. C07D 487/04; C07D 487/14
[52] U.S. Cl. .................................. 544/252; 544/245; 544/247
[58] Field of Search ................. 544/252, 247; 424/251

[56] References Cited

U.S. PATENT DOCUMENTS 3,141,043  7/1964  McBee .......................... 564/250
4,220,771  9/1980  Hermecz et al. ............... 544/252
4,234,586  11/1980 Hermecz et al. ............... 424/251

FOREIGN PATENT DOCUMENTS 847011   4/1977  Belgium .
849542   6/1977  Belgium .
883219   9/1980  Belgium .
2812586  9/1978  Fed. Rep. of Germany .
3017564  11/1980 Fed. Rep. of Germany .

OTHER PUBLICATIONS

Mosby, Heterocyclic Systems With Bridgehead Nitrogen Atoms, vol. 2, 1153-1159, Interscience Publishers Inc., New York, 1961.
Chem. Ber. 68, 2221, 1935.
J. Chem. Soc., 4694, 1956.
Chem. Ber. 95, 2182, 1962.
J. Am. Chem. Soc., 99, 2306-2309, 1979.
Smith, "The Chemistry of Open-Chain Organic Nitrogen Compounds", vol. II, pp. 172, 207, W. A. Benjamin, Inc., New York, (1966).

Primary Examiner—Donald G. Daus
Assistant Examiner—Diana G. Rivers
Attorney, Agent, or Firm—Karl F. Ross; Herbert Dubno

[57] ABSTRACT

Intermediates useful in the preparation of Rutecarpine and Rutecarpine derivatives are disclosed as well as a process for the preparation of said intermediates having the following formula:

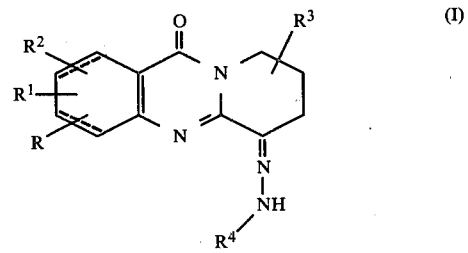

wherein R, $R^1$ and $R^2$ are the same or different and stand for hydrogen, halogen, nitro, carboxy, nitrile, alkoxy containing 1 to 4 carbon atoms, alkoxycarbonyl containing 1 to 4 carbon atoms in the alkoxy group, alkyl containing 1 to 4 carbon atoms, amino or hydroxy or R and $R^1$ together stand for methylenedioxy, $R^2$ stands for hydrogen, $R^3$ represents hydrogen or alkyl containing 1 to 4 carbon atoms, $R^4$ stands for phenyl, phenyl substituted by 1 to 3 same or different substituents selected from the group of halogen(s), alkyl, and alkoxy containing 1 to 4 carbon atoms, phenyloxy, hydroxy, nitro, amino, cyano, carboxy, alkoxycarbonyl having 1 to 4 carbon atoms, alkanoyl having 1 to 4 carbon atoms, methylenedioxy, trifluoromethyl, phenyl and dialkylamino having 1 to 4 carbon atoms in the alkyl part or naphthyl and the dotted line indicated an optional double bond. Also pharmaceutically acceptable acid addition and quaternary ammonium salts are disclosed.

9 Claims, No Drawings

6-HYDRAZONO-PYRIDO[2,1-b] QUINAZOLINE-11 ONES

The present invention relates a new 6-hydrazone-pyrido[2,1-b] quinazoline-11-ones and salts thereof, to geometrical and optical isomers and tautomers thereof, as well as to a process for the preparation of same.

The new compounds may be used as starting materials for the preparation of Rutecarpine alkaloids having Rutecarpine-like activity.

Pyrido[2,1-b] quinazoline-11-ones are known partly as alkaloids (Chem. Comm. 267, 1965; Austral J. Chem. 151, 1966; Chem. Ber. 68, 2221, 1935; J. Chem. Soc. 4694, 1956; Chem. Ber. 95, 2182, 1962 and partly as compounds with favorable pharmacological properties (DE-PS 2 812 585), BE-PS 849 542 and BE-PS 847 011.

The compounds of the formula

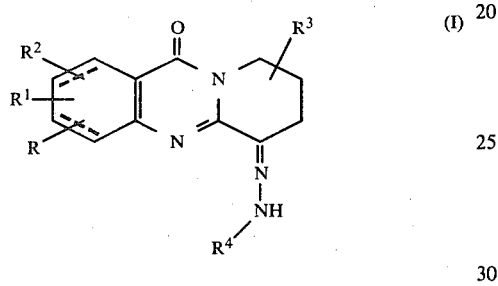

are new pyrido [2,1-b] quinazoline-11-ones. The known pyrido [2,1-b] quinazoline-11-ones are disclosed in Moshy: Heterocyclic Systems with Bridgehead Nitrogen Atoms, Vol. 2, 1153–1159, Interscience Publishers, Inc. New York, 1961.

According to the invention the new pyrido [2,1-b]-quinazoline-11-ones and acid addition salts, geometric and optical isomers thereof—wherein R, $R^1$, $R^2$ are the same or different and stand for hydrogen, halogen, nitro, carboxy, nitrile, alkoxy containing 1 to 4 carbon atoms, alkoxycarbonyl containing 1 to 4 carbon atoms in the alkoxy group, alkyl containing 1 to 4 carbon atoms, amino or hydroxy or R and $R^1$ together stand for methylenedioxy, $R^2$ stands for hydrogen, $R^3$ represents hydrogen or alkyl containing 1 to 4 carbon atoms, $R^4$ stands for phenyl, phenyl substituted by 1 to 3 of the same or different substituents selected from the group of halogen(s), alkyl, and alkoxy containing 1 to 4 carbon atoms, phenyloxy, hydroxy, nitro, amino, cyano, carboxy, alkoxycarbonyl having 1 to 4 carbon atoms, methylenedioxy, trifluoromethyl, phenyl and dialkylamino having 1 to 4 carbon atoms in the alkyl part; or naphthyl and the dotted line indicates an optional double bond may be prepared by (a) reacting a pyrido [2,1-b] quinazoline-11-one derivative of the formula

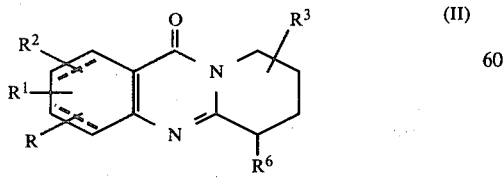

wherein R, $R^1$, $R^2$, $R^3$ and the dotted line are as given above and $R^6$ is hydrogen or formyl—with a diazonium salt of the formula $$R^4-N_2^{\oplus}Cl^{\ominus} \quad \text{(III)}$$

wherein $R^4$ stands for a phenyl group optionally substituted by 1 to 3 of the same or different substituents selected from the group of halogen(s), alkyl containing 1 to 4 carbon atoms, alkoxy having 1 to 4 carbon atoms, phenyloxy, hydroxy, nitro, amino, cyano, carboxy, alkoxycarbonyl having 1 to 4 carbon atoms in the alkoxy part, alkanoyl having 1 to 4 carbon atoms, methylenedioxy, trifluoromethyl, phenyl and dialkylamino having 1 to 4 carbon atoms in the alkyl group of naphthyl—in order to prepare compounds of the formula I—wherein $R^4$ stands for phenyl optionally substituted by 1 to 3 same or different substituents selected from halogen(s), alkyl having 1 to 4 carbon atoms, alkoxy containing 1 to 4 carbon atoms, phenyloxy, hydroxy, nitro, amino, cyano, carboxy, alkoxycarbonyl having 1 to 4 carbon atoms in the alkoxy part, alkanoyl having 1 to 4 carbon atoms, methylenedioxy trifluoromethyl, phenyl and dialkylamino having 1 to 4 carbon atoms in the alkyl group: or naphthyl and R, $R^1$, $R^2$, $R^3$ and the dotted line are as defined above or (b) reacting a pyrido [2,1-b] quinazoline-11-one derivative of the formula

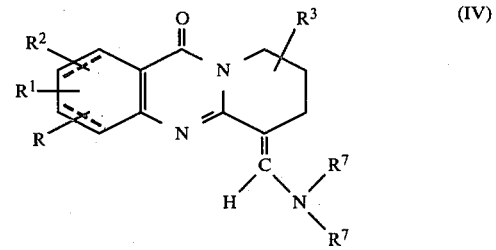

wherein R, $R^1$, $R^2$, $R^3$ and the dotted line are as given above and $R^7$ represents an alkyl group of 1 to 4 carbon atoms—with a diazonium salt of the formula III—wherein $R^4$ is as defined above—in order to prepare compounds of the formula I—wherein $R^4$ stands for phenyl optionally substituted by 1 to 3 of the same or different substituents selected from halogen(s), alkyl having 1 to 4 carbon atoms, alkoxy having 1 to 4 carbon atoms, phenyloxy, hydroxy, nitro, amino, cyano, carboxy, alkoxybarbonyl having 1 to 4 carbon atoms in the alkoxy part, alkanoyl having 1 to 4 carbon atoms, methylenedioxy, trifluoromethyl, phenyl and dialkylamino having 1 to 4 carbon atoms in the alkyl group, or naphthyl and R, $R^1$, $R^2$, $R^3$ and the dotted line are as given above, or (c) reacting a pyrido [2,1-] quinazoline-11-one-derivative of the formula

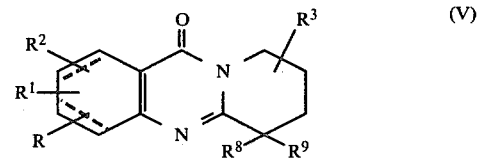

wherein R, $R^1$, $R^2$, $R^3$ and the dotted line are as given above and $R^8$ stands for hydrogen or halogen and $R^9$ is halogen—with a hydrazine derivative of the formula

 (VI)

wherein $R^4$ is as given above—and converting, if desired, a compound of the formula I containing an acid group thus obtained with a base into a salt or converting a compound of the formula I with acid into an acid addition salt or liberating a compound of the formula I from its salt formed with an acid or base.

Process variant (a) i.e. the reaction of the compound of the formula II with the diazonium salt of the formula III is conducted according to (Parmerter: Org. Reactions, 10, p. 1-142, 1959; Phillips: Org. reactions 10, p. 143-178, 1959).

According to a preferred embodiment of the process the reaction is conducted below 50° C., preferably at −10° to 20° C. The components may be added by adding a given compound of the formula II to the solution of the diazonium salt of the formula III or the other way around. The components are preferably used in an equimolar amount, but one of the components may optionally be used in a small excess. The reaction may be conducted preferably in aqueous medium, if desired in the presence of a water-miscible inert organic solvent.

As inert organic solvent alkane carboxylic acids, preferably acetic acid, propionic acid, acid amides, preferably N, N-dimethyl-formamide, alcohols, preferably methanol, ethanol, propanol, isopropanol, ketones such as acetone, methyl ethyl ketone, aromatic bases, preferably pyridine may be employed. The reaction is preferably carried out in the presence of an acid binding agent. As acid binding agent alkali alkanoates, preferably sodium acetate, potassium acetate or alkali hydroxides, preferably sodium hydroxide, potassium hydroxide or alkali carbonates, preferably sodium carbonate, potassium carbonate, or sodium bicarbonate is used.

According to process variant (b) a compound of the formula IV is reacted with a diazonium salt of the formula III. A preferred embodiment is the same as process variant (a).

According to process variant (c) a compound of the formula V is reacted with a hydrazine of the formula VI. As a compound of the formula V preferably such compounds may be used which contain chlorine or bromine as halogen in place of $R^8$ and $R^9$. Compounds of the formula V and VI are preferably reacted in the presence of an inert solvent. As inert solvents alkanols, preferably methanol, ethanol, propanol, iso-propanol etc. alkane-carboxylic acids, preferably acetic acid, propionic acid, acid amides, such as N, N-dimethyl-formamide, aromatic bases, preferably pyridine may be used. The enumerated solvents may optionally be admixed with water and then the reaction is conducted in a mixture of water and a water-miscible organic solvent. If desired an acid binding agent may be employed. As acid binding agent, the substances given for the process variant (a) may be employed. An excess of the hydrazine of the formula VI may also serve as the acid binding agent. According to a preferred embodiment of the process 1 to 8 moles, particularly preferably 2.5 to 4.5 moles of hydrazine of the formula VI may be used for 1 mole of the compound of the formula V. The reaction can be conducted at a temperature from 0° C. to 160° C.; when a solvent is used the reaction is preferably carried out at the boiling point of the solvent or solvent mixture. The reaction time may change from 30 minutes to 10 hours depending upon the reactants. Compounds of the formula I obtained in the course of process variants (a), (b) or (c) precipitate from the reaction mixture or precipitate upon aqueous dilution and can be isolated by filtration, centrifuging or other conventional methods.

The compounds of the formula I form salts with organic or inorganic acids, thus salts such as hydrochloride, hydrobromide, sulphate, phosphate, perchlorate, maleate, acetate etc. may be prepared.

Compounds of the formula I containing at least one carboxyl group form salts with bases, such as alkali metal salts, e.g. sodium or potassium salts, alkali earth metal salts, such as calcium or magnesium salts, or salts of tertiary amines, such as triethyl amine salts or ethanol amine salts etc.

The present invention includes the preparation of optical and geometrical isomers and tautomers thereof. Optical isomerism occurs when in the formula I $R^3$ is other than hydrogen. The structure of the geometrical isomers is illustrated by the formulae IA

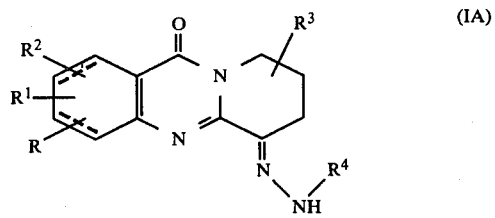 (IA)

and IB

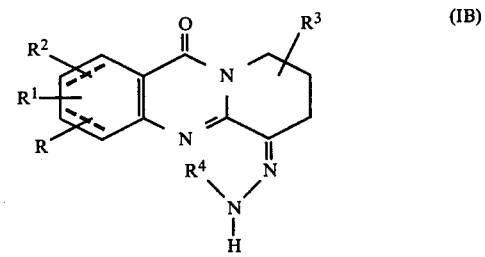 (IB)

The structure of the possible tautomers is shown by the reaction scheme A

Reaction scheme A

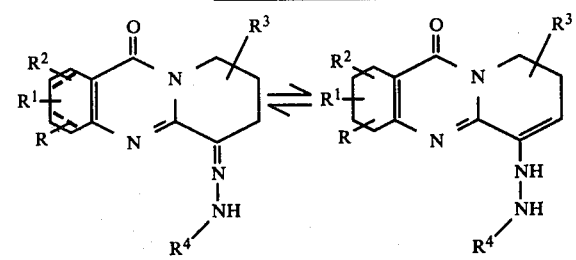

-continued
Reaction scheme A

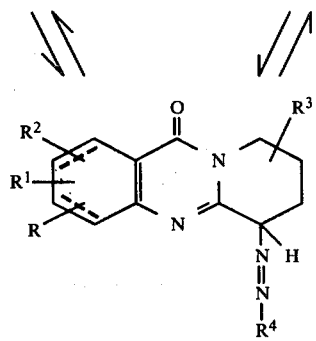

A compound of the formula I may be set free from its salts formed with an acid or base by methods known per se.

An obtained compound of the formula I may be converted to an acid addition salt by reacting same with an organic or inorganic acid. The salt formation may be performed by methods known per se comprising reacting a compound of the formula I with a corresponding acid in molar equivalent amount or in excess in the presence of an inert organic solvent.

Compounds of the formula I containing a carboxyl group may be converted to salts by reacting same with a suitable base, such as alkali metal hydroxide, alkali earth metal hydroxide, or an organic amine by methods known per se.

Most of the starting materials are known. Starting materials of the formulae II, IV and V are disclosed: Kokai Tokkyo Koho 78 130 435 and BE-PS 849 542 and 847 011 and DE-PS 2 812 585 and 2 812 586; Mosby: Heterocyclic Systems with Bridgehead Nitrogen Atoms, Vol. 2, p. 1153–1159, Interscience Publishers, Inc. New York, 1961, Him. Geterocycl. Soed. 1976, 1564–1569, 1979, 684–691 or may be prepared by methods disclosed in the above mentioned reference.

Compounds of the formula I are intermediate products of Rutecarpine alkaloids and Rutecarpine derivatives.

The Rutecarpine alkaloids and Rutecarpine analogs have Rutecarpine-like activity and are especially effective diuretics. The Rutecarpine alkaloids and Rutecarpine derivatives have the following formula:

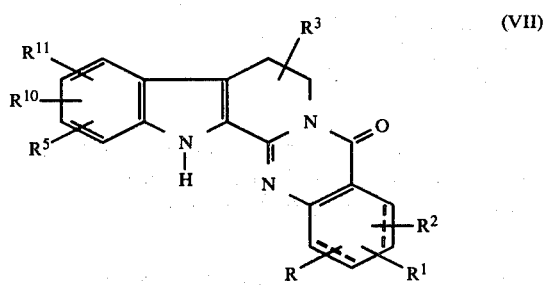
(VII)

wherein $R^5$, $R^{10}$ and $R^{11}$ are the same or different and are each hydrogen, halogen, $C_1$ to $C_4$ alkyl, $C_1$ to $C_4$ alkoxy, phenyl, cyano, trifluoromethyl, $C_1$ to $C_4$ acyl, nitro, carboxy, $C_2$ to $C_5$ alkoxycarbonyl, amino $C_1$ to $C_4$ acylamino, phenyloxy, hydroxy, $C_1$ to $C_4$ alkylamino, $C_1$ to $C_4$ alkyl substituted by dialkylamino, carbamoyl, $C_7$ to $C_{12}$ aryloxy, carbohydrazido, alkylaminocarbonyl having 1 to 4 carbon atoms in the alkyl group or dialkylamino having 1 to 4 carbon atoms in the alkyl groups. Optionally $R^5$ and $R^{10}$ together form a methylenedioxy or a —(CH=CH—)$_2$ moiety attached to two adjacent atoms of the benzene ring.

The compounds of the formula (VII) or pharmaceutically acceptable acid addition salts thereof are prepared by treating a compound or a pharmaceutically acceptable acid addition salt thereof of the formula (I) with an acid. Any acid may be used to convert the compound of formula (I) to the compound of the formula (VII). Any organic acid, inorganic acid or in fact any substance defined as a Lewis acid. Preferred inorganic acids include phosphoric acid, polyphosphoric acid, hydrochloric acid, hydrobromic acid, and sulfuric acid. Preferred organic acids include alkane carboxylic acids, for instance, acetic acid, propionic acid, or caproic acid. Preferred compounds having the ability to accept a pair of electrons and which are hence classified as Lewis acids include acid metal halides such as aluminum chloride and zinc chloride.

The temperature of the reaction to convert the compound of the formula (I) to the compound of the formula (VII) is between 30° C. and 220° C., preferably between 140° C. and 210° C., and more preferably between 160° C. and 200° C.

As a solvent alkanols such as methanol, aromatic hydrocarbons such as benzene, ethers such as diethyl ether, and halogenated hydrocarbons such as carbon tetrachloride can be used. The reaction runs for a period time 5 minutes to 120 minutes.

Further details of the invention are illustrated by the following Examples which serve merely for illustration and not for limitation.

EXAMPLES 1–22

0.1 mole of each aniline-derivative is admixed with 5 ml. of 28 V/W % of hydrochloric acid solution of 1:1 dilution and the mixture is cooled to −5° C. A solution of 0.69 g. (0.01 mole) sodium nitrite in 5 ml. of water is slowly added dropwise under steady stirring and cooling. The reaction mixture is then stirred for 30 minutes at a temperature ranging from −5° C. to 0° C., whereafter the pH of the reaction mixture is adjusted to pH=4 by adding sodium acetate. The mixture is diluted with 5 ml. glacial acetic acid and a solution of 2.0 g. (0.01 mole) 11-oxo-6,7,8,9-tetrahydro-11H-pyrido[2,1-a]quinazoline in 10 ml. of 50 Vol % acetic acid is added dropwise. The reaction mixture is stirred for 3 hours at −5° C. to 0° C. The mixture is then allowed to stand overnight in a refrigerator. The precipitated crystals are filtered and washed with water. The obtained 6-phenylhydrazono-11-oxo-6,7,8,9-tetrahydro-11H-pyrido[2,1-b]quinazolines are purified if necessary by recrystallization from n-propanol. The prepared compounds are summarized in Table 1.

EXAMPLES 23–24

One may proceed as disclosed in Examples 1 to 22 but as starting material 11-oxo-1,2,3,4,6,7,8,9-octahydro-11H-pyrido[2,1-b]quinazoline is used instead of 11-oxo-6,7,8,9-tetrahydro-11H-pyrido[2,1-b]quinazoline.

The prepared compounds are summarized in Table 2.

TABLE 1

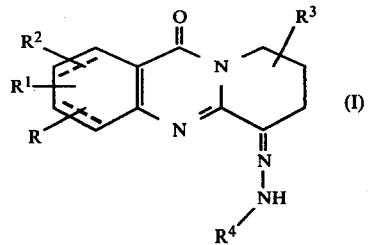

| Example | R | R¹ | R² | R³ | R⁴ | Mp. | Yield % | Empirical formula | Analysis % calculated C | H | N | found C | H | N |
|---|---|---|---|---|---|---|---|---|---|---|---|---|---|---|
| 1 | H | H | H | H | Ph | 182–184 | 90 | $C_{18}H_{16}N_4O$ | 71.03 | 5.29 | 18.41 | 70.97 | 5.27 | 18.28 |
| 2 | H | H | H | H | 4-Cl—Ph | 191–192 | 94 | $C_{18}H_{15}N_4OCl$ | 63.81 | 4.46 | 16.53 | 64.01 | 4.57 | 16.25 |
| 3 | H | H | H | H | 4-Me—Ph | 187–188 | 88 | $C_{19}H_{18}N_4O$ | 71.67 | 5.69 | 17.59 | 72.13 | 5.60 | 17.48 |
| 4 | H | H | H | H | 4-Br—Ph | 180–183 | 84 | $C_{18}H_{15}N_4OBr$ | 56.41 | 3.94 | 14.61 | 56.24 | 3.85 | 14.51 |
| 5 | H | H | H | H | 4-CF₃—Ph | 195–197 | 83 | $C_{19}H_{15}N_4OF_3$ | 61.28 | 4.06 | 15.04 | 61.89 | 4.12 | 14.86 |
| 6 | H | H | H | H | 4-PhO—Ph | 178–180 | 83 | $C_{24}H_{20}N_4O_2$ | 72.71 | 5.08 | 14.13 | 72.50 | 4.96 | 14.07 |
| 7 | H | H | H | H | 3-Cl—Ph | 181–183 | 89 | $C_{18}H_{15}N_4OCl$ | 63.81 | 4.46 | 16.53 | 63.95 | 4.58 | 16.65 |
| 8 | 3-Cl | H | H | H | Ph | 219–222 | 65 | $C_{18}H_{15}N_4OCl$ | 63.81 | 4.46 | 16.53 | 63.84 | 4.56 | 16.71 |
| 9 | 3-Cl | H | H | H | 4-Cl—Ph | 227 | 64 | $C_{18}H_{14}N_4OCl_2$ | 58.08 | 3.79 | 15.05 | 58.04 | 3.73 | 14.72 |
| 10 | H | H | H | 9-Me | Ph | 185–186 | 75 | $C_{19}H_{18}N_4O$ | 71.67 | 5.69 | 17.59 | 71.52 | 5.66 | 17.53 |
| 11 | H | H | H | H | 1-naphthyl | 192–193 | 86 | $C_{22}H_{18}N_4O$ | 70.57 | 4.84 | 14.96 | 70.55 | 4.84 | 14.40 |
| 12 | H | H | H | H | 2-naphthyl | 220 | 96 | $C_{22}H_{18}N_4O$ | 70.57 | 4.84 | 14.96 | 70.33 | 4.65 | 14.87 |
| 13 | H | H | H | H | 4-Ac—Ph | 255 | 81 | $C_{20}H_{18}N_4O_2$ | 69.34 | 5.23 | 16.17 | 69.33 | 5.35 | 16.28 |
| 14 | 3-Cl | H | H | H | 4-Me—Ph | 231 | 64 | $C_{19}H_{17}N_4OCl$ | 58.72 | 4.65 | 14.42 | 58.88 | 4.78 | 15.18 |
| 15 | H | H | H | H | 4-HO—Ph | 225/b/ | 84 | $C_{18}H_{17}N_4O_2Cl$ | 60.59 | 4.80 | 15.70 | 60.69 | 4.85 | 15.86 |
| 16 | H | H | H | H | 4-MeO—Ph | 223 | 92 | $C_{19}H_{19}N_4O_2Cl$ | 61.53 | 5.16 | 15.10 | 62.10 | 5.23 | 14.90 |
| 17 | H | H | H | H | 4-NO₂—Ph | 250/b/ | 92 | $C_{18}H_{16}N_5O_3Cl$ | 56.17 | 4.18 | 18.19 | 56.04 | 4.19 | 18.89 |
| 18 | H | H | H | H | 4-F—Ph | 245 | 90 | $C_{18}H_{16}N_4OFCl$ | 60.25 | 4.49 | 15.61 | 60.59 | 4.46 | 15.02 |
| 19 | H | H | H | H | 4-HOOC—Ph | 298/b/ | 91 | $C_{19}H_{16}N_4O_3$·HCl | 59.30 | 4.45 | 14.55 | 59.39 | 4.60 | 14.52 |
| 20 | H | H | H | H | 3-pyridyl | 188 | 23 | $C_{17}H_{15}N_5O$·HCl | 59.74 | 4.72 | 20.49 | 59.97 | 4.65 | 20.51 |
| 21 | H | H | H | H | 4-CN—Ph | 217 | 82 | $C_{19}H_{15}N_5O$·HCl | 62.38 | 4.41 | 19.14 | 62.24 | 4.50 | 19.32 |
| 22 | 2-MeO | 3-MeO | H | H | Ph | 230/b/ | 66 | $C_{20}H_{20}N_4O_3$ | 65.92 | 5.53 | 15.37 | 65.72 | 5.26 | 15.21 |

TABLE 2

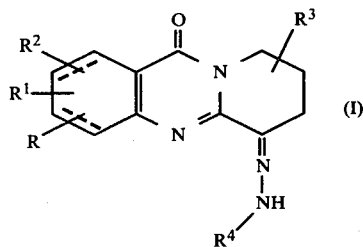

| Example | R | R¹ | R² | R³ | R⁴ | Mp. | Yield | Empirical formula | Analysis % calculated C | H | N | found C | H | N |
|---|---|---|---|---|---|---|---|---|---|---|---|---|---|---|
| 23 | H | H | H | H | Ph | 205–208 | 85 | $C_{18}H_{20}N_4O$ | 70.10 | 6.53 | 18.16 | 69.93 | 6.51 | 18.07 |
| 24 | H | H | H | 9-Me | Ph | 190–193 | 83 | $C_{19}H_{22}N_4O$ | 70.78 | 6.87 | 17.37 | 70.55 | 6.91 | 17.27 |

EXAMPLES 25

10.8 g. (0.03 mole) 6,6-Dibromo-6,7,8,9-tetrahydro-11-oxo-11H-pyrido[2,1-b]quinazoline and 13.0 g. (0.12 mole) of phenyl hydrazine are heated in 120 ml ethanol for 4 hours. The precipitated crystals are filtered after cooling. When evaporating the mother liquor further crystals are precipitating, which are filtered and washed with some alcohol. The combined filtered product is suspended in 150 ml. of water containing 8.4 g. (0.06 mole) of sodium acetate whereafter it is filtered and washed with water. 8.4 g. (81%) of 6-phenylhydrazone-6,7,8,9-tetrahydro-11-oxo-11H-pyrido[2,1-b]quinazoline are obtained which after recrystallization from isopropanol melts at 177°–179° C. and which does not give a degression of melting point when admixed with the product according to Example 1.

EXAMPLE 26

3.74 g (0.01 mole) of 6,6-dibromo-9-methyl-11-oxo-6,7,8,9-tetrahydro-11H-pyrido[2,1-a]quinazoline and 4.32 g. (0.04 mole) of phenyl hydrazine are heated in 40 ml. of ethanol for 10 hours. The precipitated crystals are filtered after cooling. The filtered product is suspended in 100 ml. water containing 2.72 g. (0.02 mole), sodium acetate, filtered and washed with water. 2.4 g. (75%) orange 6-phenylhydrazono-9-methyl-11-oxo-6,7,8,9-tetrahydro-11H-pyrido[2,1-b]quinazoline are obtained which after recrystallization from ethanol melts at 185°–187° C.

Analysis for the formula C₁₉H₁₈N₄O; calculated: C 71.67%, H 5.69%, N 17.59%; found: C 71.62%, H 5.58%, N 17.55%.

EXAMPLE 27

2.79 g. (0.01 mole) of 6-bromo-11-oxo-6,7,8,9-tetrahydro-11H-pyrido[2,1-b]quinazoline and 2.16 g. (0.02 mole) of phenyl hydrazine are heated in 30 ml. of ethanol for 6 hours at 80° C. Ethanol is then concentrated to a third volume. The mixture is then allowed to crystallize in an ice-box. The precipitated yellow crystals are filtered, and washed with ethanol and water. 2.1 g. (69%) of 6-phenyl-hydrazono-11-oxo-6,7,8,9-tetrahydro-pyrido-[2,1-b]quinazoline are obtained, which after recrystallization from isopropanol melts at 179°–180° C. which when admixed with the product according to Example 1 or Example 25 does not give any melting point degression.

Analysis for the formula C₁₈H₁₆N₄O; calculated: C 71.03%, H 5.29%, N 18.41%; found: C 70.88%, H 5.25%, N 18.38%.

EXAMPLE 28

0.93 g. (0.9 ml., 0.01 mole) of aniline are dissolved in 5 ml. 38 V/W % of hydrochloric acid of 1:1 dilution and the solution is cooled to −5° C. A solution of 0.55 g. (0.01 mole) sodium nitrite in 5 ml. water is added dropwise under steady cooling and stirring. The reaction mixture is stirred for 30 minutes at a temperature of −5° C. to 0° C. whereafter the pH of the solution is adjusted to pH=4 by adding sodium acetate and it is diluted with 10 ml. of acetic acid. To the solution of the diazonium salt a solution of 2.55 g. of 9-(dimethylamino-methylene)-11--oxo-6,7,8,9-tetrahydro-11H-pyrido[2,1-b]quinazoline hydrochloride in 25 ml. of dimethylformamide is slowly added dropwise at −5° C. The reaction mixture is stirred at 0° C. for 3 hours whereafter it is allowed to stand overnight in an ice-box. The mixture is then diluted with water and the precipitated crystals are filtered and washed with water. 2.61 g (86%) of 6-phenyl-hydrazono-6,7,8,9-tetrahydro-11-oxo-11H-pyrido[2,1-b]-quinazoline are obtained which after recrystallization from iso-propanol melts at 182°–184° C., and the product does not give any melting point degression when admixed with the product according to Example 1.

Analysis for the formula C₁₈H₁₆N₄O; calculated: C 71.03%, H 5.29%, N 18.41%; found: C 70.93%, H 5.24%, N 18.33%.

EXAMPLE 29

0.93 g. (0.01 mole) of aniline are dissolved in 5 ml. of 38 V/W % hydrochloric acid of a dilution of 1:1 and it is cooled to −5° C. A solution of 0.69 g. (0.01 mole) of sodium nitrite in 5 ml. of water is added dropwise under steady stirring and cooling. The reaction mixture is stirred for half an hour at −5° C. to 0° C. whereafter the pH of the solution is adjusted to pH=4 by adding sodium acetate and the solution is diluted with 10 ml. of acetic acid. To the reaction mixture a solution of 2.28 g. (0.01 mole) of 6-formyl-11-oxo-6,7,8,9-tetrahydro-11H-pyrido[2,1-b]quinazoline in 30 ml. of acetic acid is slowly added dropwise. The mixture is stirred for 1 hour at a temperature below 0° C. and the solution is then allowed to stand in the refrigerator. The precipitated crystals are filtered and washed with water. 3.1 g. (91%) of 6-phenyl-hydrazono-6,7,8,9-tetrahydro-11-oxo-11H-pyrido[2,1-b]-quinazoline-hydrochloride are obtained melting at 255° C.

Analysis on the basis of C₁₈H₁₇N₄OCl; calculated: C 63.60%, H 5.04%, N 16.48%, Cl 10.16%; found: C 63.44%, H 4.98%, N 16.59%, Cl 10.11%.

EXAMPLES 30 to 33

One may proceed as disclosed in Example 1–22 and as starting materials in Example 30 as pyrido[2,1-b]quinazoline derivative 2,3,4-trimethoxy-11-oxo-6,7,8,9-tetrahydro-11H-pyrido[2,1-b]quinazoline and in Example 31, 11-oxo-6,7,8,9-tetrahydro-11H-pyrido[2,1-b]quinazoline-2-carboxylic acid and in Example 32 ethyl-11-oxo-6,7,8,9-tetrahydro-11H-pyrido(2,1-b)quinazoline 2-carboxylate and in Example 33 11-oxo-6,7,8,9-tetrahydro-11H-pyrido[2,1-b]quinazoline is used and 6-phenylhydrazono 11-oxo-6,7,8,9-tetrahydro-11H-pyrido[2,1-b]quinazolines according to Table 3 are obtained. The products are recrystallized from n-propanol.

EXAMPLES 34 to 44

One may proceed as disclosed in Examples 23 to 24 and as starting materials 11-oxo-1,2,3,4,6,7,8,9-octahydro-11H-pyrido[2,1-b]quinazolines are used which result in 6-phenyl-hydrazono-4-oxo-1,2,3,4,6,7,8,9-octahydro-11H-pyrido-[2,1-b]quinazolines according to Table 4.

In Examples 42 and 43 crystals precipitated from the diazo-coupling reaction mixture are suspended in a 5% V/W % sodium hydroxide solution and the aqueous solution is shaken out with chloroform. The chloroform solution dried above anhydrous sodium sulphate is evaporated and the residue is crystallized.

EXAMPLE 45

0.46 g. (0.005 mole of aniline are dissolved in 3 ml. of hydrochloric acid (36 V/W %) of a dilution of 1:1 and the solution is cooled to −5° C. A solution of 0.35 g. (0.005 mole) of sodium nitrite in 3 ml. of water is added dropwise. The reaction mixture is stirred for half an hour at −5° C. to 0° C. whereafter the pH of the solution is adjusted to 4 by adding sodium acetate. To the reaction mixture a solution of 1.23 g. (0.005 mole) of 6-formyl-11-oxo-1,2,3,4,6,7,8,9-octahydro-11H-pyrido-[2.1-b]quinazoline in 15 ml. 75 V % acetic acid is slowly added dropwise and the solution is stirred for 3 hours at a temperature below 0° C. whereafter the mixture is allowed to stand overnight in a refrigerator and diluted with 30 ml. water. The precipitated crystals are filtered and washed with water. 1.3 g. (73%) of 6-phenyl-hydrazono-11-oxo-1,2,3,4,6,7,8,9-octahydro-11H-pyrido[2.1-b] quinazoline-hydrochloride are obtained melting at 242°–244° C.

Analysis for the formula C₁₉H₂₃N₄OCl; calculated: C 63.59%, H 6.46%, N 15.61%, Cl 9.88%; found: C 63.21%, H 6.28%, N 15.75%, Cl 9.651%.

TABLE 3

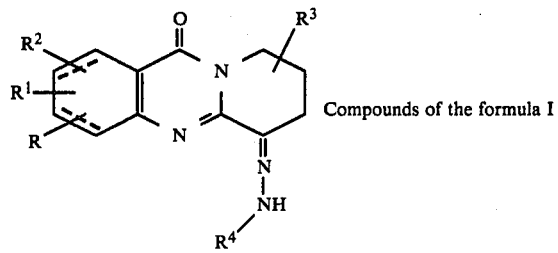

Compounds of the formula I

| Example | R | R¹ | R² | R³ | R⁴ | Mp. | Yield % | Empirical formula | Analysis % calculated C | H | N | found C | H | N |
|---|---|---|---|---|---|---|---|---|---|---|---|---|---|---|
| 30. | 2-OMe | 3-OMe | 4-OMe | H | Ph | 187-77 | 77 | $C_{21}H_{22}N_4O_4$ | 63.94 | 5.62 | 14.20 | 64.03 | 5.88 | 14.28 |
| 31. | 2-COOH | H | H | H | Ph | 257/b/ | 30 | $C_{19}H_{16}N_4O_3$ | 65.51 | 4.62 | 16.08 | 65.55 | 4.66 | 16.01 |
| 32. | 2-COOEt | H | H | H | Ph | 201 | 85 | $C_{21}H_{20}N_4O_3$ | 67.00 | 5.35 | 14.88 | 67.03 | 5.45 | 14.85 |
| 33. | H | H | H | H | 4-EtOOC—Ph | 214 | 92 | $C_{21}H_{20}N_4O_3$ HCl | 61.09 | 5.09 | 13.57 | 61.25 | 4.99 | 13.58 |

TABLE 4

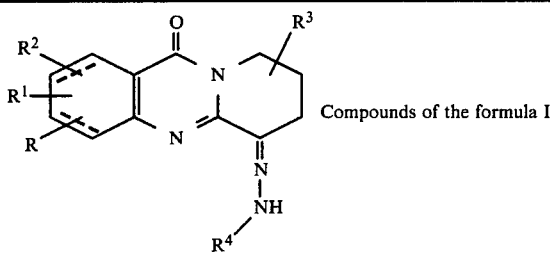

Compounds of the formula I

| Example | R | R¹ | R² | R³ | R⁴ | Mp. | Yield % | Empirical formula | Analysis % calculated C | H | N | found C | H | N |
|---|---|---|---|---|---|---|---|---|---|---|---|---|---|---|
| 34. | H | H | H | H | 4-Cl—Ph | 220 | 73 | $C_{18}H_{19}N_4OCl$ | 63.06 | 5.59 | 16.34 | 63.24 | 5.51 | 16.32 |
| 35. | H | H | H | 9-Me | 4-Cl—Ph | 207-208 | 70 | $C_{19}H_{21}N_4OCl$ | 63.95 | 5.93 | 15.70 | 64.14 | 6.17 | 15.78 |
| 36. | H | H | H | 9-Me | 4-NO₂—Ph | 168-170 | 79 | $C_{19}H_{21}N_5O_3HCl$ | 56.50 | 5.49 | 17.34 | 56.15 | 5.44 | 17.00 |
| 37. | H | H | H | H | 4-Me—Ph | 203-204 | 46 | $C_{19}H_{22}N_4O$ | 70.78 | 6.88 | 17.38 | 70.63 | 6.56 | 17.17 |
| 38. | H | H | H | 9-Me | 4-Me—Ph | 187-188 | 74 | $C_{20}H_{24}N_4O$ | 71.40 | 7.19 | 16.65 | 71.17 | 6.96 | 16.72 |
| 39. | H | H | H | 9-Me | 4-Et—Ph | 154-155 | 49 | $C_{21}H_{26}N_4O$ | 71.97 | 7.48 | 15.99 | 71.58 | 7.52 | 16.03 |
| 40. | H | H | H | 9-Me | 4-MeO—Ph | 161-162 | 42 | $C_{20}H_{24}N_4O_2$ | 68.16 | 6.86 | 15.90 | 68.43 | 6.95 | 15.80 |
| 41. | H | H | H | 9-Me | 2-naphthyl | 177-179 | 11 | $C_{23}H_{24}N_4O$ | 74.17 | 6.50 | 15.04 | 74.13 | 6.40 | 14.72 |
| 42. | H | H | H | 8-Me | Ph | 219 | 59 | $C_{19}H_{22}N_4O$ | 70.78 | 6.87 | 17.37 | 70.83 | 6.82 | 17.40 |
| 43. | H | H | H | 9-Me | 3,5-diCl—Ph | 227-228 | 33 | $C_{19}H_{20}N_4OCl_2$ | 58.33 | 5.15 | 14.31 | 58.40 | 5.23 | 14.27 |
| 44. | H | H | H | 7-Me | Ph | 200 | 59 | $C_{19}H_{22}N_4O$ | 70.78 | 6.87 | 17.37 | 70.91 | 6.75 | 17.45 |

Other compounds of the formula (I) according to the invention include (±)-6-phenyl-hydrazono-9-methyl-11-oxo-6,7,8,9-tetrahydro-11H-pyrido(2,1-b)quinoxaline-3-carboxylic acid; 6-phenylhydrazono-11-oxo-6,7,8,9-tetrahydro-11H-pyrido(2,1-b)quinoxaline-3-carboxylic acid, and (±)-6-phenylhydrazono-9-methyl-11-oxo-6,7,8,9-tetrahydro-11H-pyrido(2,1-b)-quinoxaline-2-carboxylic acid.

The following compounds are Rutecarpine derivatives of formula (VII) having Rutecarpine-like activity and are especially useful as diuretics.

EXAMPLE 46

1 g. of 6-[(4-Methyl-phenyl)-hydrazono]-6,7,8,9-tetrahydro-11H-pyrido [2,1-b] quinazoline-11-one is added in small portions to 10 g. of polyphosphoric acid heated to 180° C. within 5 minutes. After adding the above substance the reaction mixture is stirred for 30 minutes at 180° C. After cooling the mixture is diluted to 40 ml. of water and the pH of the solution is adjusted to 5 by adding 25 V/W% ammoniumhydroxide solution. The precipitated crystals are filtered and washed with water. After drying the product is dissolved in dimethylformamide and treated with active charcoal at 100° C. The dimethylformamide solution is diluted with water whereafter yellowish-white crystals are obtained which are filtered and washed with water. After drying 0.6 g. (63%) of 10-methyl-7,8-dihydro-5H,13H-indolo [2',3';3,4]-pyrido [2,1-b] quinazoline-5-one are obtained.

Analysis for the formula $C_{19}N_{15}N_3O$; calculated: C 75.72%, H 5.01%, N 13.94%; found: C 75.43%, H 4.99%, N 14.05%.

EXAMPLE 47

1 g. 6-[(4-Chloro-phenyl)-hydrazono]-6,7,8,9-tetrahydro-11H-pyrido [2,1-b] quinazoline-11-one is added to 10 g. of polyphosphoric acid heated to 180° C. and the mixture is stirred for 20 minutes at this temperature. After cooling the mixture is diluted with 40 ml. of water and the precipitate is filtered and washed with water.

After drying the product is recrystallized from a mixture of dimethylformamide and ethyl acetate. 0.77 g. (81%) 10-chloro-7,8-dihydro-5H,13H-indolo[2'3';3,4]-pyrido [2,1-b] quinazoline-5-one are obtained melting at 310° C. to 312° C.

Analysis for the formula $C_{18}H_{12}N_3OCl$; calculated: C 67.19%, H 3.76%, N 13.05%, Cl 11.01%; found: C 67.11%, H 3.74%, N 13.13%, Cl 10.97%.

EXAMPLE 48

1 g. 6-[4-Fluoro-phenyl)-hydrazono]-6,7,8,9-tetrahydro-11H-pyrido[2,1-b]quinazoline-11-one is converted according to Example 47 and 0.75 g. (79%) of 10-fluoro-7,8-dihydro-5H,13H-indolo[2',3';3,4]pyrido[2,1-b] quinazoline-5-one are obtained melting at 290° C.

Analysis for the formula $C_{18}H_{12}N_3OF$; calculated: C 70.81%, H 3.96%, N 13.76%; found: C 70.70%, H 3.94%, N 13.91%.

EXAMPLE 49

1 g. 6-[(4-Bromo-phenyl)-hydroazono]-6,7,8,9-tetrahydro-11H-pyrido[2,1-b] quinazoline-11-one is converted and processed according to Example 47 and 0.85 g. of the title product are obtained which is dissolved in 10 ml. of dimethylformamide and treated with active charcoal and applied to a column containing 15 g. of Kieselgel of particle size 0.1–0.2 mm and eluted with ethyl acetate. 0.64 g. (67%), of yellowish-white crystals of 10-bromo-7,8-dihydro-5H,13H-indolo[2',3';3,4-]pyrido-2,1-b] quinazoline-5-one are obtained melting at 284° C.

Analysis for the formula $C_{18}H_{12}N_3OBr$; calculated: C 59.03%, H 3.30%, N 11.47%; found: C 59.09%, H 3.22%, N 11.28%.

EXAMPLE 50

1 g. of 6-[(4-Cyano-phenyl)-hydrazono]-6,7,8,9-tetrahydro-11H-pyrido[2,1-b]quinazoline-11-one is heated in 10 g. of polyphosphoric acid at 180° C. for 30 minutes. After cooling the reaction mixture is diluted with 40 ml. of water and the pH is adjusted to 5 by adding 25 V/W% ammonium hydroxide solution. The precipitated product is filtered, washed with water and dried. 0.88 g. (92%) of 10-cyano-7,8-dihydro-5H,13H-indolo[2',3';3,4]-pyrido[2,1-b]quinazoline-5-one are obtained which after recrystallization from dimethylformamide melts at 255° C.

Analysis for the formula $C_{19}H_{12}N_4O$; calculated: C 73.06%, H 3.87%, N 17.93%; found: C 72.95%, H 3.86%, N 17.90%.

EXAMPLE 51

1 g. of 6-(2-Naphthyl-hydrazono)-6,7,8,9-tetrahydropyrido [2,1-b]quinazoline-11-one is converted according to Example 50 and 0.85 g. (89%) of 7,8-dihydro-5H,13H-indolo[2',3';2,3]pyrido [2,1-b]quinazoline-5-one are obtained melting at 298° C.

Analysis for the formula $C_{22}H_{15}N_3O$; calculated: C 78.32%, H 4.48%, N 12.45%; found: C 78.51%, H 4.60%, N 12.21%.

EXAMPLE 52

1 g. 6-[(4-Phenyloxy-phenyl)-hydrazono]-6,7,8,9-tetrahydro-pyrido[2,1-b]quinazoline-11-one is added to 15 g. of polyphosphoric acid heated to 180° C. and the mixture is maintained at this temperature for 20 minutes. After cooling the reaction mixture is diluted with 50 ml. of water and during cooling the pH is adjusted to 5 by adding a 25 V/W% ammonium hydroxide solution. The precipitated product is filtered and washed with water. After drying the mixture dissolved in 5 ml. dimethylformamide is applied to a column of diameter of 1 cm. filled with 15 g. of Kieselgel of particle size 0.1–0.2 mm and eluted with ethyl acetate. 0.4 g. (41%) of 10-phenyloxy-7,8-dihydro-5H,13H -indolo[2',3';3,4-]pyrido[2,1-b]quinazoline-5-one are obtained which after recrystallization from ethyl acetate melts at 276°–278° C.

Analysis for the formula $C_{24}H_{17}N_3O_2$; calculated: C 75.97%, H 4.51%, N 11.07%; found: C 76.09%, H 4.55%, N 11.02%.

EXAMPLE 53

10 g. of 6-phenyl-hydrazono-1,2,3,4,6,7,8,9-octahydro-pyrido[2,1-b]quinazoline-11-one are added to 100 g. of polyphosphoric acid heated to 180° C. and the reaction mixture is heated for 30 minutes at this temperature until the gas evolution ceases. The mixture is then cooled to room temperature and diluted with 200 ml. of water under steady cooling. The pH of the solution is adjusted to 5 by adding a 25 V/W% ammonium hydroxide solution. The precipitated product is filtered and washed with water. After drying 8.8 g. (93%) of 5-oxo-1,2,3,4,7,8-hexahydro-5H,13H-indolo[2',3';3,4-]pyrido[2,1-b]-quinazoline are obtained which after recrystallization from ethyl acetate melts at 259°–261° C.

Analysis for the formula $C_{18}H_{17}N_3O$; calculated: C 74.20%, H 5.88%, N 14.42%; found: C 74.08%, H 5.84%, N 14.48%.

EXAMPLE 54

1 g. of 6-(4-Methyl-phenylhydrazono)-9-methyl-1,2,3,4,6,7,8,9-octahydro-pyrido[2,1-b]quinazoline-11-one is added to 10 g. of polyphosphoric acid heated to 180° C. and the reaction mixture is heated for 40 minutes at this temperature. After cooling the mixture is diluted with 60 ml. of water. A yellowish-white crystalline precipitate is obtained which is filtered and washed with water. After drying the obtained solid is dissolved in chloroform and the undissolved part is filtered off. The solution is treated with active charcoal and evaporated. The obtained yellowish white oil is crystallized from ethyl acetate. 0.4 g. of 7,10-dimethyl-5-oxo-1,2,3,4,7,8-hexahydro-5H,13H-indolo[2',3';3,4]pyrido [2,1-b]quinazoline are obtained melting at 220° C.

Analysis for the formula $C_{20}N_{21}N_3O$; calculated: C 75.20%, H 6.62%, N 13.15%; found: C 75.11%, H 6.70%, N 13.22%.

EXAMPLE 55

1 g. 9-Methyl-6-(4-chloro-phenylhydrazono)-1,2,3,4,6,7,8,9-octahydro-pyrido[2,1-b]quinazoline-11-one is added to 10 g. of polyphosphoric acid heated to 180° C. and the reaction mixture is heated for 30 minutes at this temperature. The reaction mixture is cooled when the gas evolution ceases and diluted with 40 ml. of water whereupon a yellowish white precipitate is formed. The precipitated product is filtered and washed with water. After drying the product is crystallized from ethanol. 0.7 g. of 7-methyl-10-chloro-5-oxo-1,2,3,4,7,8-hexahydro-5H,13H-indolo[2',3';3,4-]pyrido[3,2-a]quinazoline are obtained melting at 248° C.

Analysis for the formula $C_{19}N_{18}N_3OCl$; calculated: C 67.15%, H 5.33%, N 12.36%, Cl 10.43%; found: C 67.08%, H 5.37%, N 12.41%, Cl 10.35%.

EXAMPLE 56

1 g. of 9-methyl-6-phenylhydrazono-1,2,3,4,6,7,8,9-octahydro-pyrido[2,1-b]quinazoline-11-one is added to 15 g. of polyphosphoric acid heated to 170° C. and the mixture is stirred for 20 minutes at 180° C. After cooling the dark melt is diluted with 50 ml. of water. Greenish-yellow crystals are precipitated, which are filtered and washed with water. After drying the product is recrystallized from ethanol. 0.4 g. of 7-methyl-5-oxo-1,2,3,4,7,8-hexahydro-5H,13H-indolo[2',3';3,4]pyrido-[2,1-b]quinazoline are obtained melting at 232° C.

Analysis for the formula $C_{19}H_{19}N_3O$; calculated: C 74.72%, H 6.27%, N 13.75%; found: C 74.66%, H 6.28%, N 13.83%.

EXAMPLE 57

1 g. of 8-Methyl-6-phenylhydrazono-1,2,3,4,6,7,8,9-octahydropyrido[2,1-b]quinazoline-11-one is added to 10 g. of polyphosphoric acid heated to 180° C. and the reaction mixture is stirred for 40 minutes at 180°–185° C. The mixture is then cooled to room temperature and diluted with 50 ml. of water under cooling.

The precipitated crystals are filtered and washed with water. After drying the obtained product is dissolved in 20 ml. of chloroform and treated with active charcoal. After evaporating the chloroform solution the residual oil is crystallized from ethyl acetate. 0.6 g. of 8-methyl-5-oxo-1,2,3,4,7,8-hexahydro-5H,13H-indolo[2',3';3,4]-pyrido[2,1-b]quinazoline are obtained melting at 220°–221° C.

Analysis for the formula $C_{19}H_{19}N_3O$; calculated: C 74.72%, H 6.27%, N 13.75%; found: C 74.77%, H 6.31%, N 13.67%.

EXAMPLE 58

1 g. of 6-(3,5-Dichloro-phenylhydrazono)-9-methyl-1,2,3,4,6,7,8,9-octahydro-pyrido[2,1-b]quinazoline-11-one is added to 10 g. of polyphosphoric acid heated to 180° C. and the reaction mixture is heated for 50 minutes at 190° C. After cooling upon adding 50 ml. of water yellow precipitate is formed which is filtered and washed with water. The obtained product is crystallized from ethyl acetate after drying. 0.7 g. of 9,11-dichloro-5-oxo-1,2,3,4,7,8-hexahydro-5H,13H-indolo[2',3';3,4]pyrido-[2,1-b]quinazoline are obtained melting at 296°–297° C.

Analysis for the formula $C_{19}H_{17}N_3OCl_2$; calculated: C 60.97%, H 4.57%, N 11.22%, Cl 18.94%; found: C 60.82%, H 4.55%, N 11.10%, Cl 19.08%.

EXAMPLE 59

1000 g. of 5-oxo-1,2,3,4,7,8-hexahydro-5H,13H-indolo-[2',3';3,4]pyrido[2,1-b]quinazoline are homogenized with 1300 g. of crystalline cellulose and with 140 g. of amylopectine. The obtained homogenizate is granulated with 150 g. Eudragit lac solution, regranulated after drying at 40° C. and homogenized with a powder mixture of 20 g. magnesium stearate and 20 g. of talc. The mixture is then compressed to tablets by method known per se with adjusting the tablets to 250 mg.

EXAMPLE 60

750 mg. of 10-methyl-7,8-dihydro-5H,13H-indolo-[2',3';3,4]pyrido[2,1-b]quinazoline-5-one are homogenized with 1050 g. of crystalline cellulose and 140 g. of amylopectine. The mixture is then granulated with 150 mg. of Eudragit lac solution and after drying at 40° C. and after regranulating the mixture is homogenized with a powder mixture of 20 g. magnesium stearate and 20 g. of talc, and compressed to 200 mg. tablets.

We claim:

1. A compound of the formula

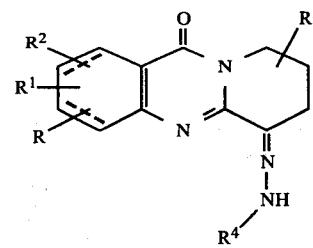

or a pharmaceutically acceptable acid addition or quaternary ammonium salt thereof
wherein R, $R^1$ and $R^2$ are the same or different and stand for hydrogen, halogen, nitro, carboxy, nitrile, alkoxy containing 1 to 4 carbon atoms, alkyl containing 1 to 4 carbon atoms, amino or hydroxy, or R and $R^1$ together stand for methylenedioxy and $R^2$ stands for hydrogen;

$R^3$ stands for hydrogen or alkyl containing 1 to 4 carbon atoms;

$R^4$ stands for phenyl, phenyl substituted by 1 to 3 of the same or different substituents selected from the group consisting of halogen, alkyl having 1 to 4 carbon atoms, alkoxy having 1 to 4 carbon atoms, phenyloxy, hydroxy, nitro, amino, cyano, carboxy, alkoxycarbonyl having 1 to 4 carbon atoms, alkanoyl having 1 to 4 carbon atoms, methylenedioxy, trifluoromethyl, phenyl and dialkylamino having 1 to 4 carbon atoms in the alkyl group, or $R^4$ is naphthyl, and the dotted line indicates an optional double bond.

2. 6-Phenylhydrazono-11-oxo-6,7,8,9-tetrahydro-11H-pyrido(2,1-b)quinazoline as defined in claim 1 or a pharmaceutically acceptable acid addition or quaternary ammonium salt thereof.

3. (±)6-Phenylhydazono-9-methyl-11-oxo-6,7,8,9-tetrahydro-11H-pyrido(2,1-b)quinazoline as defined in claim 1 or a pharmaceutically acceptable acid addition or quaternary ammonium salt thereof.

4. 6-Phenylhydrazono-11-oxo-1,2,3,4,6,7,8,9-octahydro-11H-pyrido(2,1-b)quinazoline as defined in claim 1 or a pharmaceutically acceptable acid addition or quaternary ammonium salt thereof.

5. (±) 6-Phenylhydrazono-9-methyl-11-oxo-1,2,3,4,6,7,8,9-octahydro-11H-pyrido(2,1-b)quinazoline as defined in claim 1 or a pharmaceutically acceptable acid addition or quaternary ammonium salt thereof.

6. 6-Phenylhydrazono-11-oxo-6,7,8,9-tetrahydro-11H-pyrido(2,1-b)quinazoline-2-carboxylic acid as defined in claim 1 or a pharmaceutically acceptable acid addition or quaternary ammonium salt thereof.

7. (±) 6-Phenylhydrazono-9-methyl-11-oxo-6,7,8,9-tetrahydro-11H-pyrido(2,1-b)quinazoline-2-carboxylic acid as defined in claim 1 or a pharmaceutically acceptable acid addition or quaternary ammonium salt thereof.

8. (±) 6-Phenylhydrazono-9-methyl-11-oxo-6,7,8,9-tetrahydro-11H-pyrido(2,1-b)quinazoline-3-carboxylic acid as defined in claim 1 or a pharmaceutically acceptable acid addition or quaternary ammonium salt thereof.

9. 6-Phenylhydrazono-11-oxo-6,7,8,9-tetrahydro-11H-pyrido(2,1-b)quinazoline-3-carboxylic acid as defined in claim 1 or a pharmaceutically acceptable acid addition or quaternary ammonium salt thereof.

* * * * *